(12) United States Patent
Khatri et al.

(10) Patent No.: US 8,962,784 B2
(45) Date of Patent: Feb. 24, 2015

(54) ISOCYANATE TERMINATED MACROMER AND FORMULATION THEREOF FOR USE AS AN INTERNAL ADHESIVE OR SEALANT

(75) Inventors: Chetan Anirudh Khatri, Belle Mead, NJ (US); Benjamin D. Fitz, Brooklyn, NY (US); Joseph Zavatsky, Somerville, NJ (US)

(73) Assignee: Ethicon, Inc., Somerville, NJ (US)

( * ) Notice: Subject to any disclaimer, the term of this patent is extended or adjusted under 35 U.S.C. 154(b) by 1400 days.

(21) Appl. No.: 12/339,142

(22) Filed: Dec. 19, 2008

(65) Prior Publication Data

US 2010/0158849 A1    Jun. 24, 2010

(51) Int. Cl.
| | | |
|---|---|---|
| *C08G 18/10* | (2006.01) | |
| *C08G 18/08* | (2006.01) | |
| *C08G 18/77* | (2006.01) | |
| *A61L 24/04* | (2006.01) | |
| *C08G 18/42* | (2006.01) | |

(52) U.S. Cl.
CPC ............. *C08G 18/771* (2013.01); *A61L 24/046* (2013.01); *C08G 18/10* (2013.01); *C08G 18/42* (2013.01); *C08G 18/4238* (2013.01); *A61L 2400/06* (2013.01)
USPC ................... 528/59; 528/44; 528/52; 528/53; 528/58; 528/85; 156/331.4; 156/331.7

(58) Field of Classification Search
CPC ...... C08G 18/23; C08G 18/00; C08G 18/003; C08G 18/724; C08G 18/7657
See application file for complete search history.

(56) References Cited

U.S. PATENT DOCUMENTS

| | | | |
|---|---|---|---|
| 4,829,099 A | | 5/1989 | Fuller et al. |
| 4,888,125 A | * | 12/1989 | Konig et al. ............. 252/182.21 |
| 5,260,484 A | * | 11/1993 | Hickmann et al. ............ 564/346 |
| 6,210,441 B1 | | 4/2001 | Flodin |
| 2006/0188547 A1 | | 8/2006 | Bezwada |
| 2007/0276121 A1 | | 11/2007 | Westergom et al. |

OTHER PUBLICATIONS

Avadhani, C.V., et sl., "Synthesis and Characterization of Oxyethylene containing Diisocyanates and Polyimides Therefrom", 1990, Journal of Polymer Science, 28, pp. 1681-1691.*
McMurry, John, "Organic Chemistry", 1988, $2^{nd}$ Edition, p. 1129.
Webster, Iain et al., "Adhesives for Medical Applications", Polymeric Biomaterials, Second Edition, Revised and Expanded, edited by Severian Dumitriu, (2002), p. 716.

* cited by examiner

*Primary Examiner* — Michael G Hartley
*Assistant Examiner* — Lance Rider
(74) *Attorney, Agent, or Firm* — David R. Crichton (LK)

(57) ABSTRACT

A novel macromer or mixture thereof is described herein, comprising isocyanatophenyl ether terminal moieties and at least two residues of a water-soluble polymer having a molecular weight ranging from 80 to 10,000 adjacent to the ether group of the isocyanatophenyl ether terminal isocyanate moieties, thereby forming at least two ether linkages in the macromer or mixture thereof. A method for making a polyisocyanate macromer is also described herein.

11 Claims, No Drawings

ISOCYANATE TERMINATED MACROMER AND FORMULATION THEREOF FOR USE AS AN INTERNAL ADHESIVE OR SEALANT

FIELD OF THE INVENTION

Described herein are novel polyisocyanate macromers or mixtures thereof and the use thereof to form an internal adhesive or sealant for surgical use in surgical specialties such as: cardiovascular, peripheral-vascular, cardio-thoracic, gynecological, neuro- and general abdominal surgeries. More particularly, the macromers or mixture thereof or a formulation thereof polymerizes in the human body to form an elastic gel that is biocompatible and degrades into products that are non-toxic and biocompatible. Additionally, the degradation products are water soluble, allowing for the degradation products to be eliminated from the human body as waste products.

BACKGROUND OF THE INVENTION

Generally, the key requirements of a tissue adhesive are:
(1) In use, the adhesive must mimic the mechanical performance of the undamaged tissue;
(2) The adhesive should provide sufficient tack for "primary" fixation with the opportunity for manipulation and re-alignment prior to setting strongly;
(3) Any exothermic process involved in the curing of the adhesive should not damage the surrounding tissue;
(4) The adhesive must not elicit any toxic response by the surrounding healthy tissue and should facilitate the re-growth of new tissue where possible;
(5) The adhesive should not liberate harmful degradation products;
(6) The adhesive should degrade, and as it does so, it should be replaced by new tissue with minimal scarring; and
(7) Any biodegradation products should not accumulate in the body but should be eliminated naturally either by excretion or incorporation into the natural biochemical cycle.
["Polymeric Biomaterials", $2^{nd}$ Ed., Marcel Dekker Inc., (2002) pp. 716]

It is well known in the art that diisocyanate and polyisocyanate compounds may be used to form polymeric adhesives and foams. However, many of the diisocyanate and polyisocyanate monomers that are commercially available are small molecules that present toxicity and sensitization hazards and that polymerize to form products having toxic degradation products, for instance, aromatic amines. As such, compositions containing commercially available small molecule diisocyanate and polyisocyanates are unsuitable for use inside the human body.

Metabolically acceptable polyisocyanate monomers are described in U.S. Pat. No. 4,829,099. More specifically, this reference describes an aromatic benzoyl isocyanate terminated monomer, having glycolic acid residues and polyethyleneglycol residues, in formula "I, Preferred". This reference indicates that the resultant polymer will degrade ultimately to metabolically acceptable products, including p-aminobenzoic acid, polyethylene glycol and glycolic acid. Although the resultant polymer in principal could degrade into the aforementioned compounds, it is believed that only the glycolic acid residues would hydrolyze in vivo, resulting in a mixture of water-soluble and water insoluble fragments. The water-soluble fragments would be eliminated naturally by excretion from the body. However, the water insoluble fragments would not be eliminated naturally, resulting in the undesirable accumulation of the water insoluble fragments in the body.

Published U.S. Patent Application 2007/0276121 A1 discloses macromers or a mixture thereof, comprising benzoyl isocyanate terminal moieties and at least two residues of a water-soluble polymer having one or more hydrolysable linkage that are biodegradable in vivo.

Published U.S. Patent Application 2006/0188547 A1 discloses a class of amines, isocyanates and bioabsorbable polyurethanes, polyamides and polyesterurethanes polymerized therefrom. Further it discloses means to attach moieties such as glycolic acid, lactic acid, p-dioxanone, and ε-caprolactone with phenolic amino acid, to form a new chemical entity.

Polyester-urethane-urea block copolymers prepared from commercially available small molecular diisocyanates, i.e. tolylene diisocyanate (TDI), diphenylmethane-4,4'-diisocyanate (MDI), and hexamethylene diisocyanate (HMDI), are described in U.S. Pat. No. 6,210,441. However, these copolymers would be unsuitable for use as a surgical adhesive or sealant, since the copolymers are already polymerized, i.e., already cured, and would not provide sufficient opportunity for manipulation and re-alignment. Moreover, such copolymers are not believed to mimic the mechanical performance of undamaged tissue.

Therefore, it is desirable to have a monomer based internal adhesive or sealant formulation that is capable of polymerizing in vivo to form an internal adhesive or sealant, in order to provide an opportunity for manipulation and re-alignment. Specifically, it is desirable that the adhesive or sealant formulation fills internal cavities and voids, penetrating and conforming to the interstices and pores of the tissue, prior to curing or setting.

Additionally, it is desirable to have a monomer based internal adhesive or sealant formulation that polymerizes in vivo, where the monomer, the formulation thereof, and the resultant polymer are biocompatible. The resultant polymer should also be biodegradable. The degradation products of the resultant polymer should also be both biocompatible and water soluble, so that the degradation products are completely eliminated from the human body as waste products.

SUMMARY OF THE INVENTION

Novel macromers or a mixture thereof are described herein, comprising isocyanatophenyl ether terminal moieties:

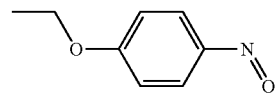

urethane-linked to absorbable compounds, such as esters of poly(ethylene glycol).

DEFINITIONS

Unless defined otherwise, all technical and scientific terms used herein have the same meaning as is commonly understood by one of skill in the art to which this invention belongs. All patents and publications mentioned herein are incorporated by reference.

"Biocompatible" as used herein refers to a material that, once implanted, does not interfere significantly with wound healing and/or tissue regeneration, and does not cause any significant metabolic disturbance.

"Biodegradable" and "bioabsorbable" as used herein refer to a material that is broken down spontaneously and/or by the mammalian body into components, which are consumed or eliminated in such a manner as not to interfere significantly with wound healing and/or tissue regeneration, and without causing any significant metabolic disturbance.

"Water-soluble polymer" as used herein refers to a polymer, which dissolves in water, forming transparent solutions under ambient conditions (e.g. body temperature).

"Polyisocyanate" as used herein refers to a compound with two or more isocyanate groups.

"Urethane linkage" as used herein refers to a residue derived from a urethane moiety and having a carbonyl-containing functional group in which the carbonyl carbon is bound both to an ether oxygen and to an amine nitrogen:

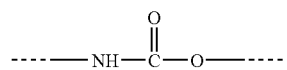

["Organic Chemistry", J. McMurry, $2^{nd}$ ed., Brooks/Cole Publishing Company, (1988), pp 1129].

"Urea linkage" as used herein refers to a residue derived from a moiety having a carbonyl-containing functional group in which the carbonyl carbon is bound to identical units of amine nitrogen:

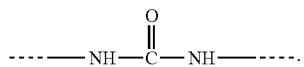

["Nomenclature of Organic Chemistry", Pergamon Press, Oxford, (1979)].

DETAILED DESCRIPTION OF THE INVENTION

The inventive composition described in this application is a biocompatible polyisocyanate macromer, terminating with isocyanatophenyl ether groups and having the structural formula I:

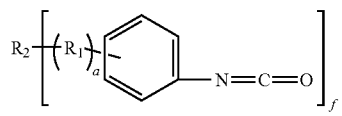

where $R_1$ is an organic residue containing an ether linkage to the aromatic moiety and a urethane linkage that is attached to $R_2$. The substitution of $R_1$ relative to NCO residue can be ortho, meta and para positions, or combinations thereof. The value of f represents the number of isocyanate residues linked to the hydroxyl group on $R_2$ on the macromer. The presence of ether group, an electron-donating group on the aromatic moiety, makes isocyanate group react slowly with water to form amine. The amine formed in this macromer is very reactive and reacts immediately with isocyanate group from another macromer thus building high molecular weight polymer useful as functional tissue sealant even from a linear (f=2) macromer.

As described above, a monomer based internal adhesive or sealant formulation that is capable of polymerizing in vivo to form an internal adhesive or sealant, should wet the tissue to which it is applied, penetrating and conforming to the interstices and pores of the tissue, prior to curing or setting. Additionally, the monomer, the formulation thereof, and the resultant polymer should be biocompatible.

The monomer and the formulation thereof described herein are suitable for internal applications, since neither the monomer, the formulation thereof nor the resultant polymer metabolizes in the human body to form toxic products.

Additionally, the monomer and the formulation thereof polymerize to form a biocompatible polymer upon contact with water or body fluids. The biocompatible polymer then degrades in vivo to form degradation products that are both biocompatible and water soluble, which are then eliminated from the human body as waste products.

The monomer and the formulation thereof have multiple medical applications and may be used in many types of surgery, including, but not limited to, cardiovascular, peripheral-vascular, cardio-thoracic, gynecological, neuro- and general abdominal surgery.

For example, the monomer and the formulation thereof may be used as an internal surgical adhesive in orthopedic procedures such as anterior cruciate ligament repair, meniscal tear repair (or as a hydrogel for the replacement of the meniscus), posterior capsule reconstruction, rotator cuff repair, and as a bone adhesive. It could also be used as an adhesive for lung volume reduction, patch fixation, subcutaneous tissue repair, and aortic dissection. In particular, it can be used as stomach adhesive for stomach volume reduction, and as adhesive for mesh fixation for hernia repair, drain fixation, valve attachment, attachment for adhesion prevention films, attachment of tissue to tissue (e.g. synthetic or biologic tissue scaffold to tissue, bioengineered tissue to tissue), tissue to device (e.g. mesh, clip, film) and device to device.

Second, the monomer and the formulation thereof may be used for subcutaneous tissue repair and for seroma prevention in procedures such as mastectomy, breast reconstruction & augmentation, reconstructive or cosmetic abdominoplasty and liposuction, face lift, C-section, hysterectomy in obese patients, orthopedic on thigh region, incisional hernia repair, lipoma excision, traumatic lesions, fistula treatment, graft fixation, and nerve repair.

Third, the monomer and the formulation thereof may be used as a sealant to attach and seal dural patch products, bile duct, bile leaks in liver bed, bladder leaks, bone graft, burn graft dressing and liquid occlusive dressing. As a sealant, it can be coated on tissue, device, and tissue-device interface and it can be used as dural—cranial sealant, dural—spine sealant, cardio/peripheral vascular sealant, GI sealant (e.g. esophagus, intestine, large organ, pancreas, stomach, and gastric ulcer), lung sealant, soft organ sealant (e.g. liver, spleen, pancreas), bonewax substitute, tumor sealant, staple/glue combination, sealant/hemostats combination, urethra sealant. It can be used in procedures including, but not limited to, gastric bypass, parenchymatous organs resection, tracheostomy, ulcerative colitis diverticulosis, radical prostatectomy, sinus reconstruction, sternotomy, choledochoduodenostomy, and gallbladder (liver) bed sealing, and cholecystectomy.

Fourth, the monomer and the formulation thereof may be used as a filler or a periurethral bulking agent in procedures including, but not limited, to dead space removal in reconstructive and cosmetic surgeries, (e.g. plastic/cosmetic/reconstructive, face/facial defect, or void filling), urinary incontinence and other gynecologic procedures, anal fissure/fistula, catheter injection into myocardium for treating congestive heart failure, nuclear augmentation, pancreatic/hepatic cyst/fistula obliteration, and pediatric esophogeal fistula.

Fifth, the monomer and the formulation thereof may be used as a matrix for tissue engineering (e.g. tissue scaffolds, delivery matrix for cells, delivery matrix for brachytherapy (radiation therapy) agents, delivery matrix for growth factors, injection matrix for in situ-forming empty cell scaffold, injection matrix for scaffold for delivery of stem cells, cell lysate, or other biologics, bioactives, pharmaceuticals, and neutraceuticals, localization matrix for chemotherapy, and localization matrix for contrast agent.

Sixth, the monomer and the formulation thereof may be used as an adhesion prevention barrier in procedures such as cardiac, open chest, general surgery, obstetrics and gynecological surgeries, orthopedic surgeries, and spine (e.g. artificial disk).

Seventh, the monomer and the formulation thereof may be used as an occluding material for embolization (e.g. GI Fistula, cerebral/vascular occlusive brain aneurism, tubal occlusion, and varicose vein occlusion).

Macromer

The composition described herein is a biocompatible polyisocyanate macromer, terminating with isocyanatophenyl ether groups and having the structural formula I:

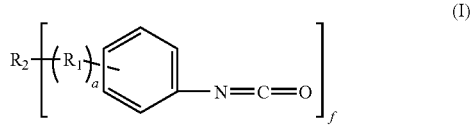
(I)

where $R_1$ is an organic residue containing a urethane linkage that is attached to $R_2$. The substitution of $R_1$ relative to NCO residue can be ortho, meta and para positions, or combinations thereof. The value of f represents the number of isocyanate residues linked to the hydroxyl group on $R_2$ on the macromer. When f=2, formula I represents a linear macromer, with two isocyanate end groups. When f is greater than 2, formula I represents a branched macromer, with more than two isocyanate end groups, while a represents the repeating units of $R_1$ and ranges from 1 to 5.

The absence of the electron-withdrawing group (e.g. C=O) in formula I (f=2) enables the linear macromers, to readily cure to form a synthetic glue upon exposure to moistures as opposed to benzoyl functionalized diisocyanate macromers described in published U.S. Patent Application 2007/0276121 A1 where the branched macromer (f>2) is desirable to obtain cured elastic high molecular weight polymer. Therefore, the increased reactivity exhibited from having the presence of the ether linkage present in the macromer in the present invention eliminates the needs of having the branched macromer as contemplated in the '121 Application. The advantages of having the ether linkage include, without limitation to, simple manufacturing process and characterization of the resulting macromers, and ease of use.

An example of $R_1$ is shown below, wherein a=1

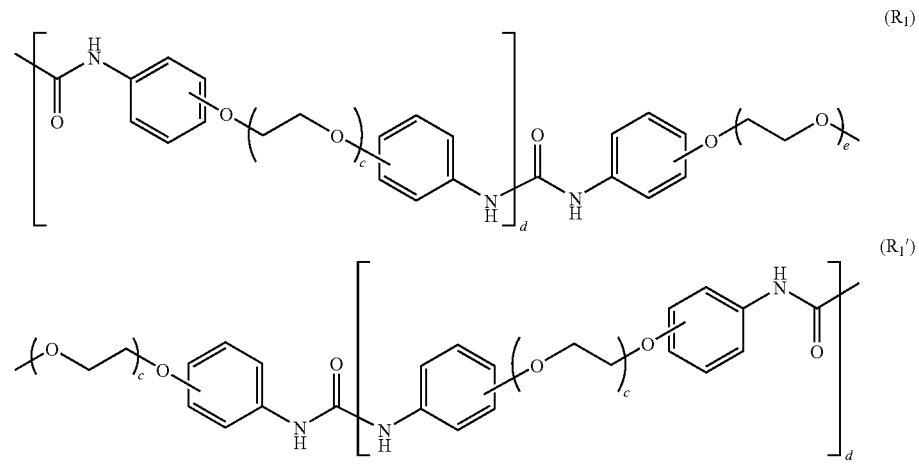

where d is the mean number of repeating di-aromatic ether linkers=within the isocyanate macromer and $0 \leq d \leq 5$; the ethylene oxide portion of $R_1$ may be linear or branched, and c, representing repeating ether unit, may range from 1 to 100, and preferably from 1 to 10.

A non-limiting example of such, wherein a=1, c=4 d=0, and f=2 is shown in Example 1 below, wherein each of the values for a, c, d and f are determined by LC-MS as described more fully in the example.

The general structure of $R_2$ in formula I is the following:

($R_2$)

where $R_2$ in formula I has one or more hydrolyzable ester linkages that are biodegradable in vivo;

$R_3$ may be residue of a water soluble polymer, including but not limited to a residue of a polyalkylene glycol such as polyethylene glycol, a polyalkylene oxide, polyvinylpyrrolidone, poly(vinyl alcohol), poly(vinyl methyl ether), polyhydroxyethyl methacrylate, a polyacrylic acid polymer and copolymer, polyoxazoline, polyphosphazine, polyacrylamide, a polypeptide, or the water-soluble derivatives of any of the above, that is capable of forming ester linkages together with $R_4$, and urethane linkages together with $R_1$ when "a" is one or more. Further, $R_3$ may be linear or branched. When $R_3$ is a polyethylene glycol residue,

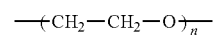

and "a" is one or more, n should be sufficiently large to render the degradation product IV (shown below) water soluble. For example, n may range from 2 to 250, preferably from 5 to 100, and more preferably is 5 to 25. The molecular weight of $R_3$ may range from 80 to 10,000, preferably 200 to 6000, and more preferably 200 to 4000. These residues of water-soluble polymer must be coupled into the macromer in the $R_3$ position and are critical to the solubility of the degradation products, as will be discussed in more detail below.

$R_4$ may be an organic residue capable of having "f" carboxylate end-groups. For example, $R_4$ may be derived from linear diacids, such as diglycolic acid, malonic acid, glutaric acid, succinic acid, adipic acid, or carboxylic acid terminated-polyalkyleneglycols such as polyalkylene glycol dicarboxylates.

If $R_4$ is an aliphatic dicarboxylate:

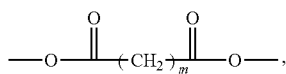

m may range from 1 to 10. The selection of m is based on two factors: biocompatibility and solubility of degradation products. If m is 0, the diacid hydrolytic degradation product of the macromer is too acidic, thus detrimental to biocompatibility of the composition. If m is too large, the diacid degradation product will no longer be water-soluble.

Alternatively, $R_4$ may be derived from a branched acid such as tricarballylic acid, citric acid, or tartaric acid or the glutaric anhydride derivative thereof. Alternately, $R_4$ may be derived from any of the aforementioned acids, carboxylic acid terminated-polyalkyleneglycols or glutaric and hydride derivative, resulting in a compound with carboxylate end-groups. Additional examples of $R_4$ are shown below:

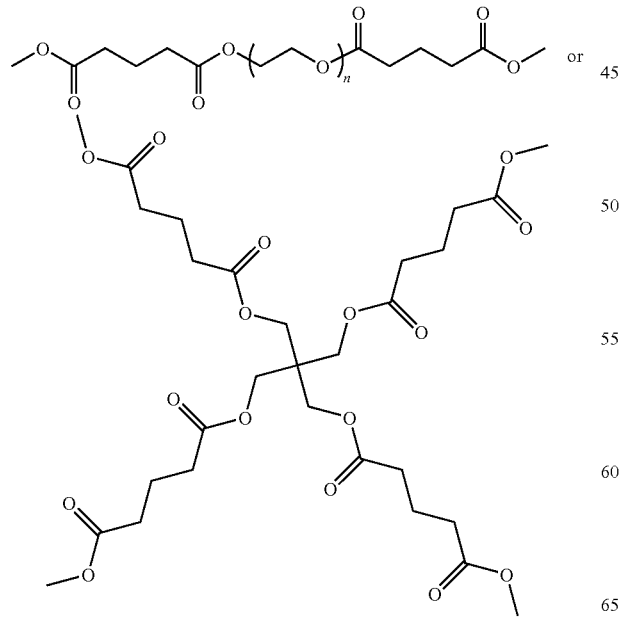

Alternately, $R_2$ may be formed from any carbonyl-containing moiety via synthetic routes (including but not limited to trans-esterification, acid halide—alcohol condensation, acid-alcohol condensation) resulting in ester linkages to $R_3$.

Examples of $R_2$ include but are not limited to a residue of a PEG-ester made from the polycondensation reaction of polyethylene glycol and a compound bearing multiple carboxylic groups, wherein the carboxylic group containing compounds include but are not limited to diglycolic acid, malonic acid, succinic acid, glutaric acid, adipic acid, tartaric acid, and carboxylic acid terminated-polyalkyleneglycols.

Examples of a PEG-ester version of $R_2$ residue include but are not limited to:

(a)

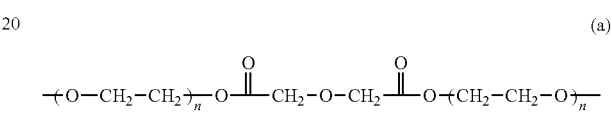

where n is 20 for PEG of Mw 900 and the diacid is diglycolic acid (b)

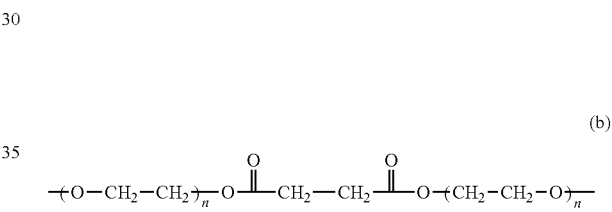

where n is 20 for PEG of Mw 900 and the diacid is succinic acid (c)

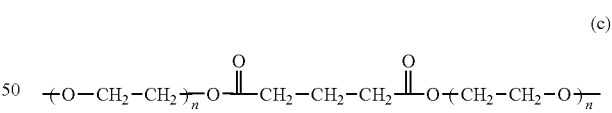

where n is 20 for PEG of Mw 900 and the diacid is glutaric acid (d)

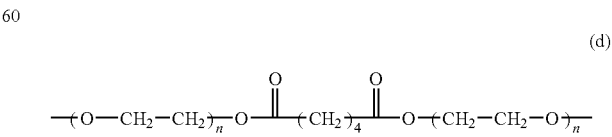

where n is 20 for PEG of Mw 900 and the diacid is adipic acid

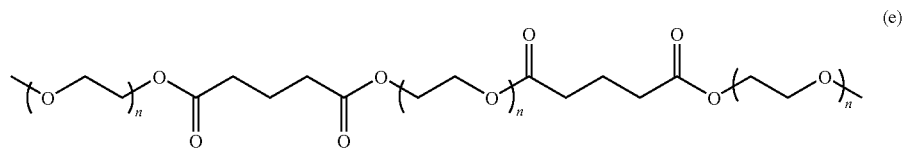
(e)
other examples include branched $R_2$ residues are shown below:
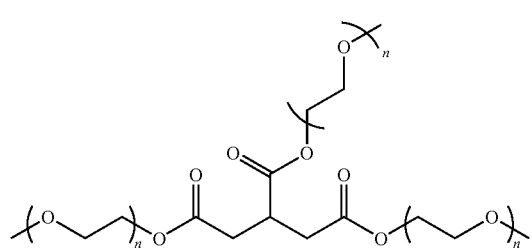
(f)
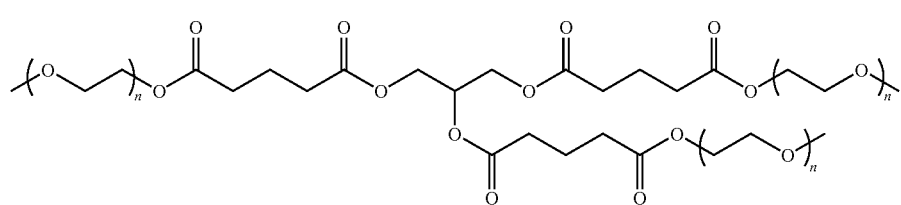
(g)
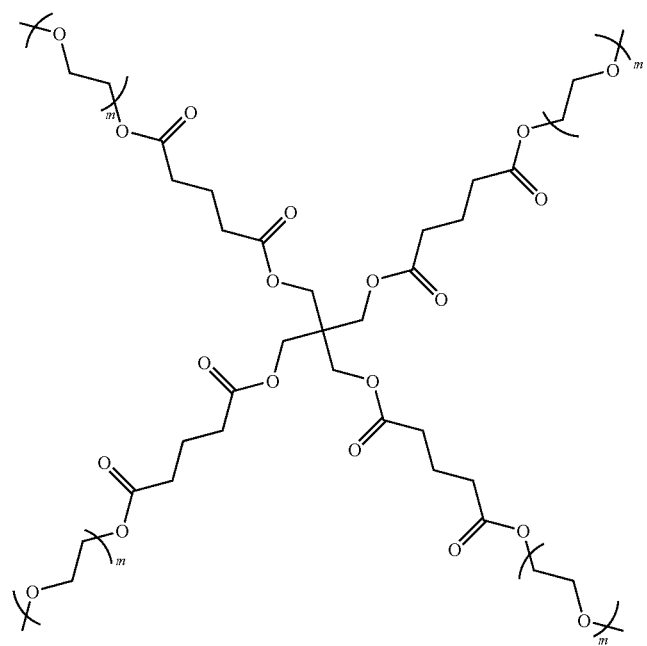
(h)
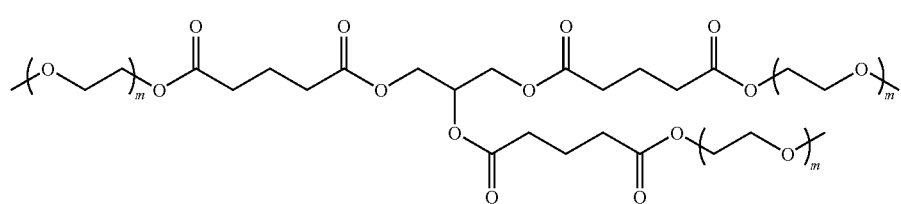
(i)

-continued

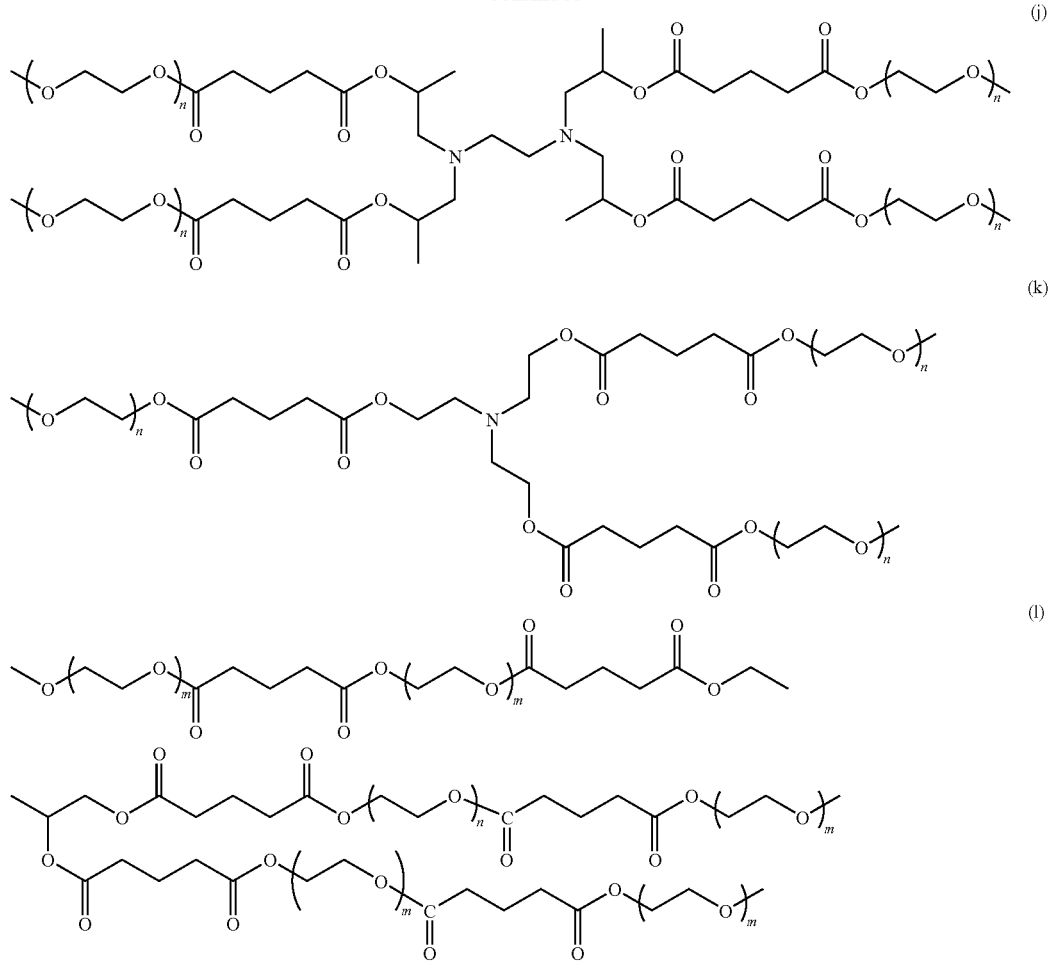

The molecular weight of the R₂ residue portion of the macromer may range from about 80 to 20,000 g/mol.

The range of the molecular weight of the macromers described herein may be between about 500 to 20,000 g/mol, and preferably between about 500 and about 4000 g/mol.

Macromer-Containing Formulation:

A medically acceptable formulation may comprise the polyisocyanate macromer, a solvent, a catalyst, a surfactant, a stabilizer or antioxidant, and a color additive.

Typically, the solvent is a hydrophilic solvent, including but not limited to dimethyl sulfoxide (DMSO), acetone, dimethoxy PEGs, glycerine, Tween 80, dimethylisosorbide, propylene carbonate, and 1-methyl-2-pyrrolidinone (NMP). Less hydrophilic solvents may also be considered, such as: ethyl lactate, triacetin, benzyl alcohol, benzylbenzoate, various ester solvents, such as: triethyl citrate, acetyltriethyl citrate, tri-n-butyl citrate, acetyltri-n-butyl citrate, ethyl acetate and the like. For example, the solvent may be used in an amount up to about 50 weight % based on the total weight of solvent and macromer.

The solvent plays several roles in the macromer formulation including: (1) viscosity control, (2) control of bubble/foam formation and bubble escape, (3) to enhance tissue penetration, and (4) to provide improved tissue wetting. The viscosity of the formulation ranges from 10 to 100,000 cp, preferably from 500 to 50,000 cp.

Surfactants may also be added to the formulation to control foaming: non-ionic surfactants such as Tween, Brij and siloxanes, as well as ionic surfactants, such as lecithin (phosphatidyl choline), sodium dodecyl sulfate, among others known in the arts.

Catalysts may also be added to the formulation for to increase reaction speed, such as triethylene diamine (DABCO), pyridine, ethyl-2-pyridyl acetate, and stannous octoate.

Color additives that may be utilized in the macromer formulation include, but are not limited to, methylene blue, FD&C Blue #1 or #2, and conventional color additives that are used in absorbable medical devices such as sutures.

Antioxidants such as butylated hydroxyl toluene (BHT) may be present in the macromer formulation to improve shelf stability of the product.

Adhesive System

One example of an adhesive system includes, but is not limited to, a system where the macromer and a solvent are stored separately until ready for use. For example, the macromer may be stored in one barrel of a double barrel syringe while the solvent is stored in the other barrel. Alternatively, the macromer and the solvent may be mixed by conventional means prior to use.

Biocompatible Elastic Gel

The resultant polymer after the in vivo polymerization of the macromer is an elastic gel that is biodegradable, and the degradation products thereof should be both biocompatible and water soluble, so that the degradation products are completely eliminated from the human body as waste products.

Specifically, the macromer or formulation thereof polymerizes to form a biocompatible elastic gel upon contact with water or body fluids, via the following reaction scheme:

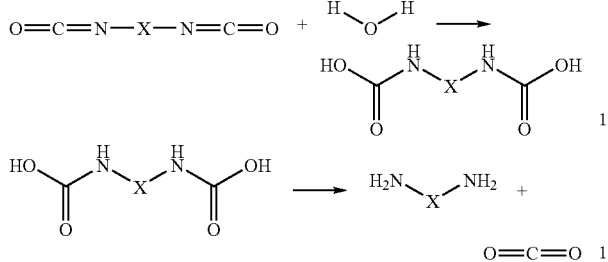

wherein X represents the structural component between the two terminal functional groups and X depends on the type of macromer (as described in figure I) utilized. The above reaction readily occurs under body conditions resulting in the spontaneous degradation of the dicarbamate to the diamine and carbon dioxide. The reactivity of the isocyanate and the subsequently formed amine can be adjusted by controlling the electron density of the reacting nitrogen moiety by substituting functional groups on the aromatic ring so as to accommodate the need of the clinical application.

In a subsequent reaction, the newly formed diamine reacts with an isocyanate group to form an elastic gel, via the following reaction scheme:

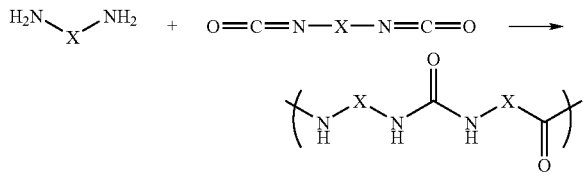

Degradation Products

The elastic gel formed from the macromer described herein is biodegradable and degrades by hydrolysis in vivo to form degradation products, including aromatic degradation products, that are both biocompatible and water soluble. In order to insure water solubility of any aromatic degradation product, the elastic gel is designed to cleave in such a way that the terminal groups on the aromatic degradation product are residues of water-soluble polymers. For example, after the macromer adhesive or sealant formulation polymerizes in the body, the elastic gel that results has the following repeat unit as shown in formula IV.

IV

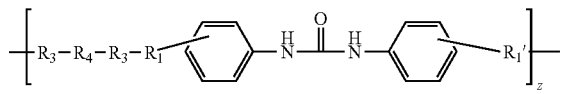

The biocompatible elastic gel (IV) that is formed comprises various hydrolysable linkages, including but not limited to, aliphatic ester linkages, urethane linkages and urea linkages. The aliphatic ester linkages in the elastic gel have a higher tendency to degrade in vivo, than the other types of linkages, thereby leaving an initial aromatic degradation product V.

V

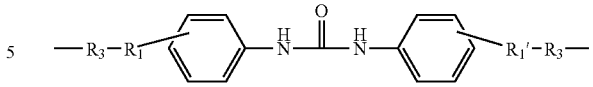

During the timeframe from implantation of the macromer adhesive or sealant formulation to excretion of the aromatic degradation product V from the body.

This composition has multiple medical applications. For example, as an internal surgical adhesive, the adhesive can bond tissue to tissue, tissue to medical device and medical device to medical device. As a sealant, the composition can be coated on a tissue, or on a medical device, or on the interface of a medical device with tissue to prevent leaks. The composition can be used to form films in situ that may have applications, such as for the prevention of surgical adhesions. The composition can be used to form foams in situ that may have applications, such as a filler (e.g. dead space removal, reconstructive and cosmetic surgeries), bulking agents, tissue engineering (e.g. scaffolds) materials and others where foams and sponges are useful. The composition can be formulated so that it is injectable and used to form gels in situ that are localized, and adherent to tissue, staying at the site where they are injected. These may have applications such as a delivery matrix for cells and other biologicals, bioactive agents and pharmaceutical or neutraceutical agents, and as embolization agents, and as means to localize contrasting agents. The composition may also be used to attach medical devices (e.g. meshes, clips and films) to tissues. This composition can be used internally in many types of surgery, including, but not limited to, cardiovascular, peripheral-vascular, cardio-thoracic, gynecological, neurological and general abdominal surgery.

As a surgical sealant/adhesive, it can be used as an adjunct to primary wound closure devices, such as staples, sutures, to seal potential leaks of gasses, liquids, or solids. More specifically, the surgical adhesive/sealant may be applied to a tissue as a part of a surgical procedure, in various forms, for example: liquid, powder, film, sponge or foam, impregnated fabric, impregnated sponge or foam, or spray.

As a filler, the macromer or formulation thereof may be used as a facial, defect or void filler. For example, the formulation may be applied in the interstices of an internal void and allowed to polymerize therein, such that the polymer fills the internal cavities and voids, penetrating and conforming to the interstices and pores of the tissue. The formulation may be used after a broad number of procedures having potential risk of dead space formation, including, but not limited to, radical mastectomy (i.e. breast and regional lymph nodes removal for cancer treatment), breast reconstruction and augmentation procedure, reconstructive or cosmetic abdominoplasty and liposuction, face-lift, cesarean section and hysterectomy in obese patients, orthopedic procedures on thigh region, incisional hernia repair, lipoma excision, and traumatic lesions, i.e. closed trauma.

While the following examples demonstrate certain embodiments of the invention, they are not to be interpreted as limiting the scope of the invention, but rather as contributing to a complete description of the invention.

EXAMPLES

Example 1

The Building Block Diisocyanate (PEG4-ether-Ar—NCO) Used in the Preparation of the Urethanes Disclosed Herein is Prepared in the Following Scheme

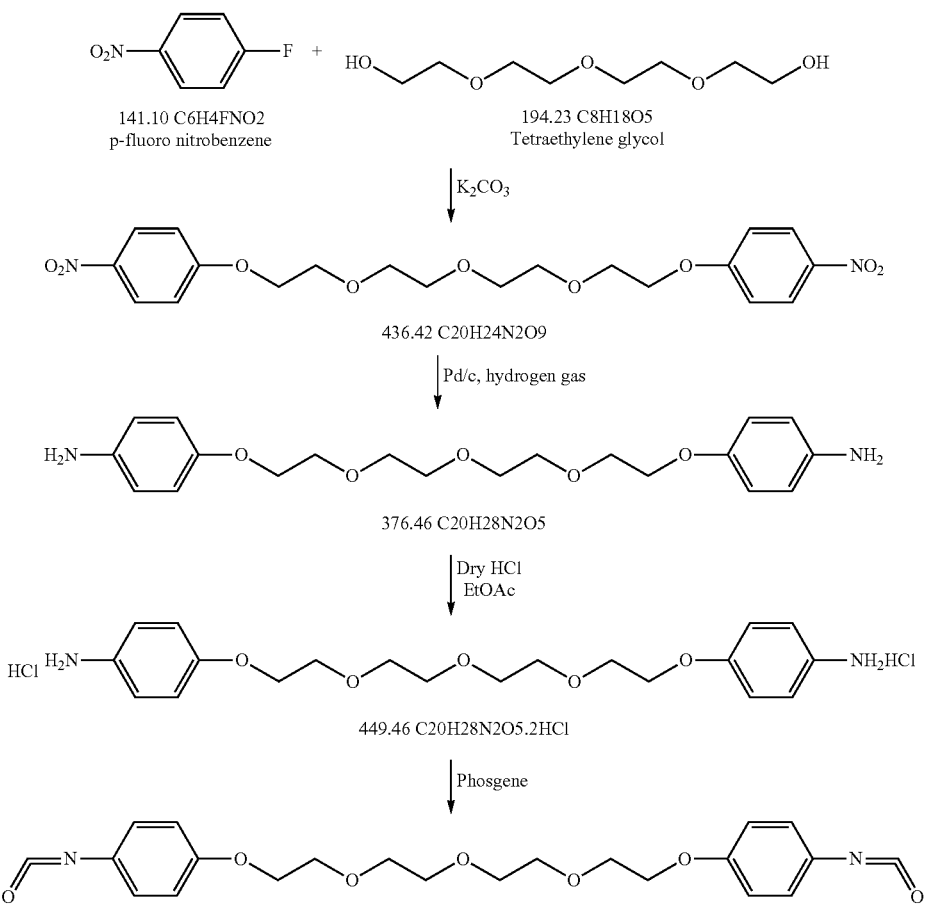

The PEG4-ether-Ar—NCO final product is a waxy brown solid at room temperature with a melting point less than 120 C. The structure is confirmed by NMR. The purity by NMR is 99.5%, the purity by HPLC is 96%.

Following the procedure described above, the ortho and meta derivatives can be synthesized starting with ortho and meta fluoro-nitrobenzene respectively.

Example 2

To Make the Absorbable PEG-ester Urethanes, the Following PEG-esters are Prepared (2.1) di-PEG400-adipate (L4Ad), Prepared from Aldrich cat #494852, lot 13009HS, purified by heating with toluene and mixing with silica-citric acid, diatomaceous earth and activated charcoal then filtering with a 2-micron cellulose paper.

(2.2) di-PEG900-glutarate (L9G)—

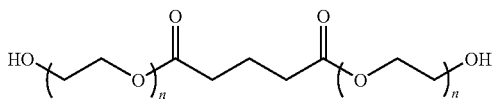

is prepared in the following manner. Into a clean dry, tared flask with stir-bar the following are weighed: 90.00 g (0.1 mol) PEG900 and 6.61 g (0.05 mol) glutaric acid. A glass pipette attached to nitrogen stream is immersed in the liquid mixture and a controlled bubbling nitrogen sparge is arranged. While temporarily stopping the nitrogen sparge, from the second neck, 0.5 g Tin (II) oxalate powder are added. When the powder is transferred, and the Tin (II) oxalate powder has been allowed to mix well into the PEG solutions for several minutes at room temperature, the nitrogen sparge is resumed, while ensuring continuous but controlled (little splashing) nitrogen bubbling into reaction mixture. The flask is then submerged in an oil bath at 180° C. The reaction is monitored for 2 hours. After 2 hours at 180° C., the glassware is quickly reconfigured and set-up to apply high vacuum with dry-ice/acetone vacuum trap. The reaction is allowed to continue at 180° C. for 16 hours under high vacuum. After 16 hours, the vacuum is released with nitrogen. The work-up of the product is described next. The oil bath is cooled to 80° C. Next the following ingredients are added: ~100 mL toluene, 5 g silica-citric acid, 5 g diatomaceous earth, and 5 g activated charcoal. The mixture is stirred for at least 2 hours, then filtered and concentrated with a rotary evaporator. The product is a waxy solid at room temperature. The product yield is 70%. The percent conversion of COOH groups is 99.5% (by titration).

(2.3) di-PEG600-PEG600-diacid (L6P6)—

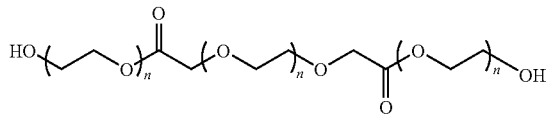

is prepared in the same manner as 2.2 above, with the following exception, the reactants are: 120.0 g (0.2 mol) PEG600 and 60.0 g (0.1 mol) PEG600diacid.

(2.4) PEG400-diglutarate-diPEG600 (L6G4—linear, PEG 600-glutarate-PEG 400-glutarate-PEG600).

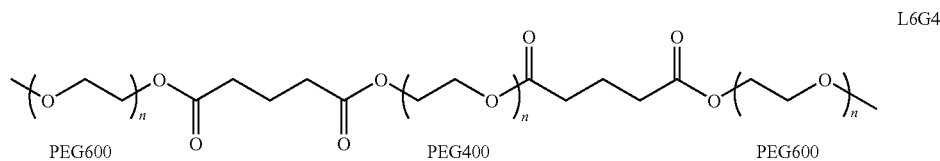

L6G4

PEG600    PEG400    PEG600

The procedure to prepare L6G4 is as follows. To a clean, dry 1 L 4-neck flask fitted with mechanical stirrer, nitrogen inlet, temperature probe and dean-stark trap is charged 149.79 g (0.3744 moles) of PEG 400. The contents are heated to 120° C. with stirring under nitrogen. Upon reaching temperature, vacuum is applied for 1.5 hours. Vacuum is released and 85.56 g (0.7499 moles) of Glutaric Anhydride is added. The solution is stirred under nitrogen at 120° C. for 2.5 hours until IR showed no anhydride present. The solution is cooled and 436.06 g (0.7268 moles) of PEG 600 NF and 0.67 g (0.0032 moles) of Tin (II) Oxalate are added. The flask is heated to 180° C. and held for 2 hours under nitrogen sparge. Vacuum is applied for an additional 16 hours after which the conversion of acid to ester groups is 99.96% based on the acid content. The polyol is cooled to 80° C. and the following are added: 6.97 g of silica-citric acid, 7.11 g of diatomaceous earth and 3.39 g of activated carbon. The slurry is stirred at 80° C. under nitrogen blanket for 1 hour. The slurry is diluted to 50% w/v in toluene and stirred for another 15 minutes and filtered through 2-micron cellulose paper. The solvent is evaporated to leave a pale yellow, viscous liquid. Yield=95%, ester conversion=99.88%, Tin content is found to be less than 5 ppm by atomic absorption spectroscopy.

Example 3

Several PEG-ester polyols are conjugated with the PEG4-ether-Ar—NCO to make isocyanate-terminated PEG-ester-urethanes at a reaction stoicheometry of 2 mol di-NCO:1 mol polyol:

(3.1) PEG4-ether-Ar—NCO-urethane-capped-L4Ad.

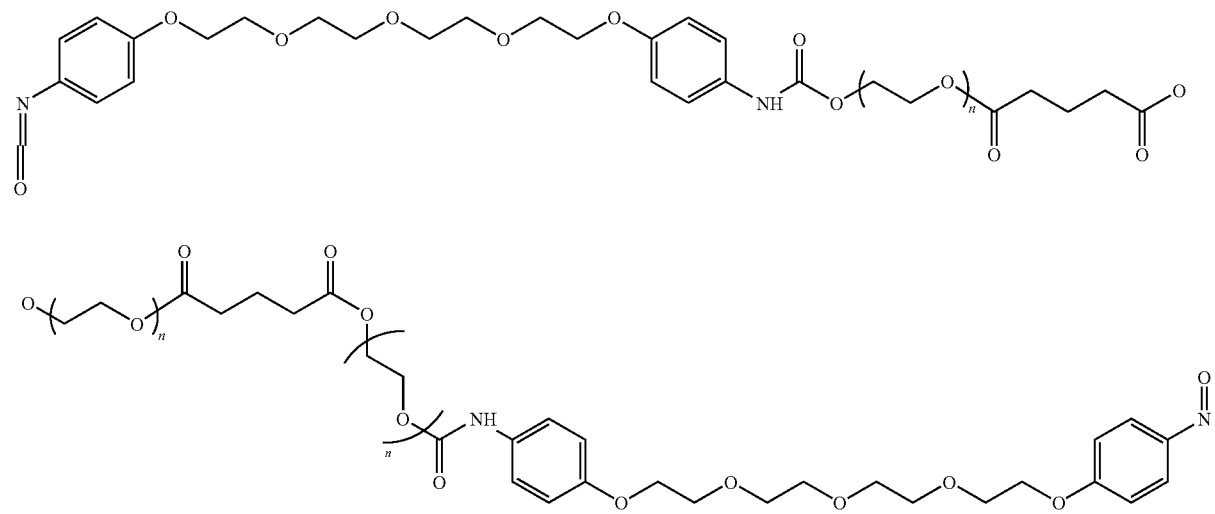

10.0 g of L4Ad are added to a round bottom flask, the flask is heated to 120° C. with high vacuum (<100 microns Hg) for 2 hours to remove traces of moisture. Next the flask is cooled to 70° C. Next 9.55 g of PEG4-ether-Ar—NCO are added under nitrogen. The mixture is stirred under nitrogen at 70° C. for 24 hours. The product is an amber colored viscous liquid. The structure is confirmed by infrared spectrometry. When formulated at 75% in acetone, the Brookfield viscosity is approximately 5000 centipoise at 25° C.

The remaining PEG-ester-urethanes are prepared in an identical manner, their compositions and description are given in Table 1, below.

TABLE 1

PEG-ester-Urethanes prepared from 2 mol of PEG4-ether-Ar-NCO to 1 mol diol.

| Example # | Polyol Description | Wt. Polyol | Wt. diNCO |
|---|---|---|---|
| 3.1 | L4Ad | 10.0 | 9.55 |
| 3.2 | L9G | 20.0 | 9.55 |
| 3.3 | L6G4 | 20.0 | 9.55 |
| 3.4 | L6P6 | 20.0 | 9.55 |

Following the procedure described above, the PEG-ester-urethanes of ortho (PEG2-ether-Ar—NCO) and meta (PEG3-ether-Ar—NCO) derivatives can be synthesized in a similar fashion.

The PEG4-Ar-ether-NCO and urethanes therefrom can be sterilized by Cobalt-60 irradiation up to 40 kGy. Upon irradiation there is no significant change in the proton NMR spectra.

The acute ex vivo performance was evaluated for these NCO-urethanes, as formulated at 75% in acetone, these data are provided in Table 2. Their chronic ex vivo performance values are shown in Table 3. These ex vivo performance data illustrate that the strength of the macromers when cured on biological tissues is more than adequate for use sealing leaks such as: cerebrospinal fluid, blood, intestinal contents and air.

TABLE 2

Summary of Acute Ex-vivo performance on PEG-ester Urethanes.

| <averages, n = 5> | 3.1 L4Ad-urethane | 3.2 L9G urethane | 3.3 L6G4 urethane | 3.4 L6P6 urethane |
|---|---|---|---|---|
| Pericardium T-Peel (N/cm) | 0.54 | na | 1.41 | na |
| Intestine T-Peel (N/cm) | 0.52 | na | 1.65 | na |
| Dura Burst (mmHg) | 24 | na | 485 | 324 |
| Intestine Burst (mmHg) | 15 | 84 | 80 | 41 |
| Artery Burst (circumferential end-end anastomosis) (mmHg) | na | 161 | 147 | na |
| Artery Burst (13-gauge needle hole defect) (mmHg) | na | na | 300 | 200 |
| Pulmonary Burst (mmHg) | na | na | 83 | 80 |

TABLE 3

Summary of chronic ex-vivo performance on PEG-ester Urethanes.

| <averages, n = 5> | | 3.3 L6G4 urethane | 3.4 L6P6 urethane | 3.2 L9G urethane |
|---|---|---|---|---|
| Dura Burst (mmHg) | 3 hr | 218 | na | 365 |
| | 6 hr | 291 | na | 230 |
| Pulmonary Burst (mmHg) | 3 hr | 120 | 19 | na |
| | 6 hr | 80 | 8 | na |
| CV/PV chronic pressure load (cycles at pressure) | | >6 hours at 240/200 mmHg | 5.8 hrs at 120/80 mmHg | na |

What is claimed is:

1. A polyisocyanate macromer or mixture of macromers of the formula:

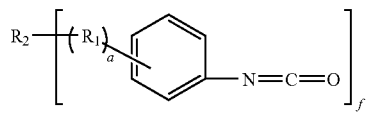

wherein f is two or more; "a" is 1 to 5 and $R_1$ is

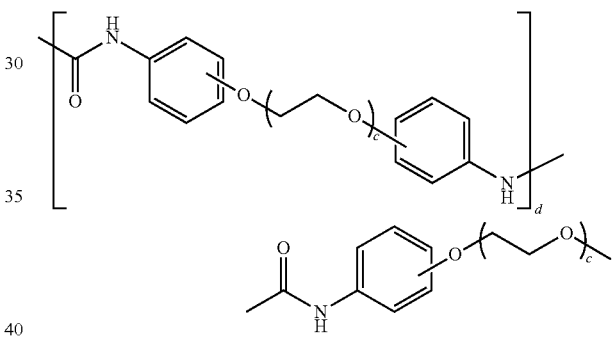

where d is a number between 0 to 5 and c is from 2 to 10; $R_2$ is

where $R_3$ is a linear or branched residue of a water soluble polymer that is capable of forming ester linkages to $R_4$, and urethane linkages to $R_1$ when "a" is one or more; and $R_4$ is a linear or branched organic residue capable of having "x" carboxylate end-groups where $2 \leq x \leq 6$; and wherein the polyisocyanate macromer or mixture of macromers form a bioabsorbable tissue sealant and/or adhesive in a moist environment.

2. The macromer or mixture of macromers of claim 1, where f is two, and the macromer is represented by the formula:

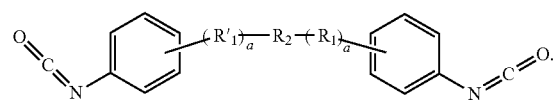

3. The macromer or mixture of macromers of claim 2, where $R_1'$ is represented by the formula:
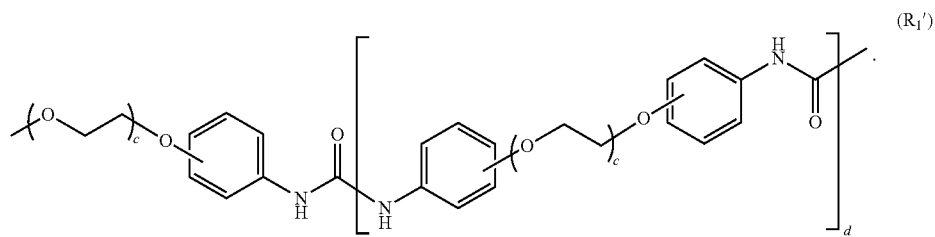
4. The macromer of claim 1, where $R_2$ is selected from the group consisting of Ben will have one more structure
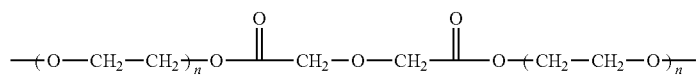
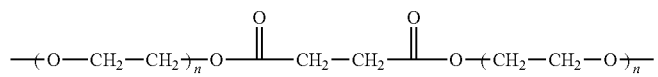
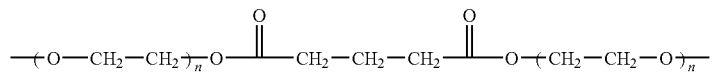
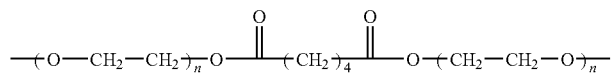
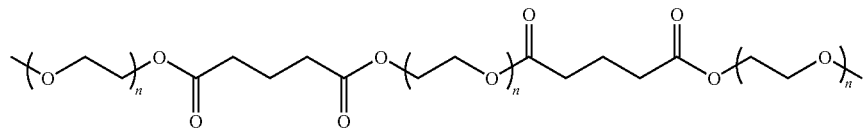
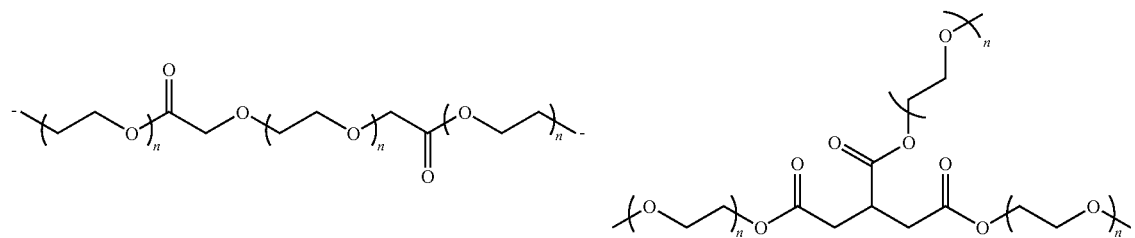
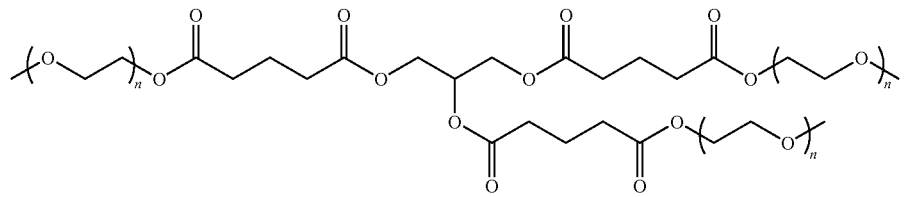

-continued
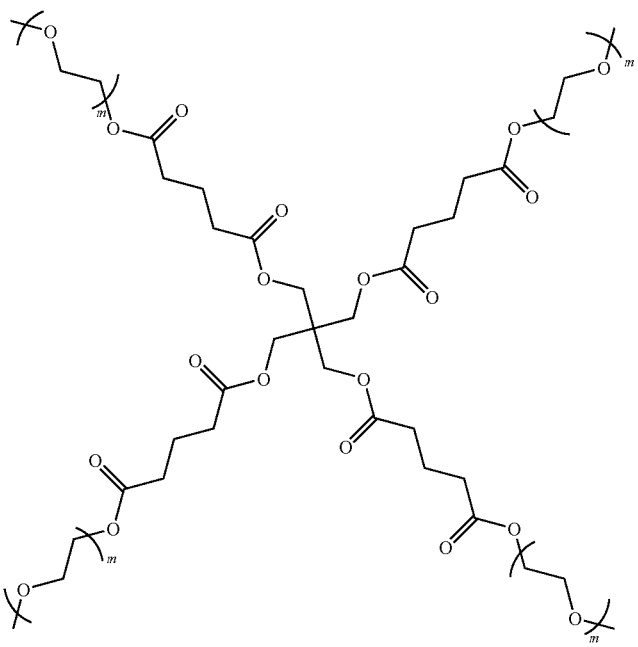
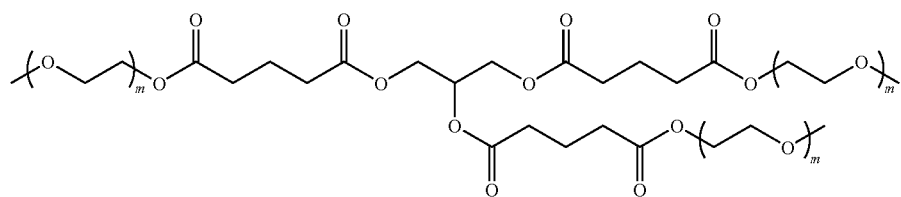
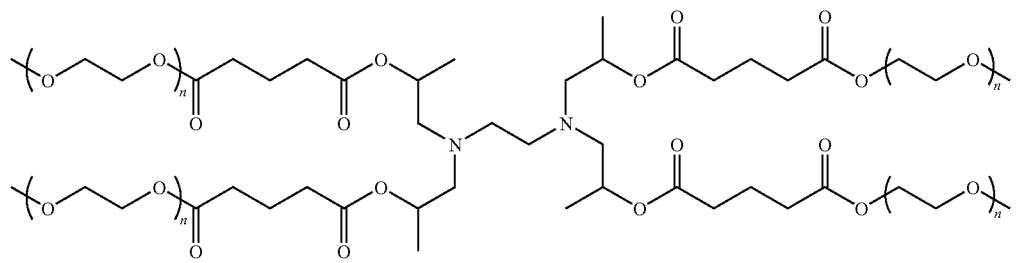
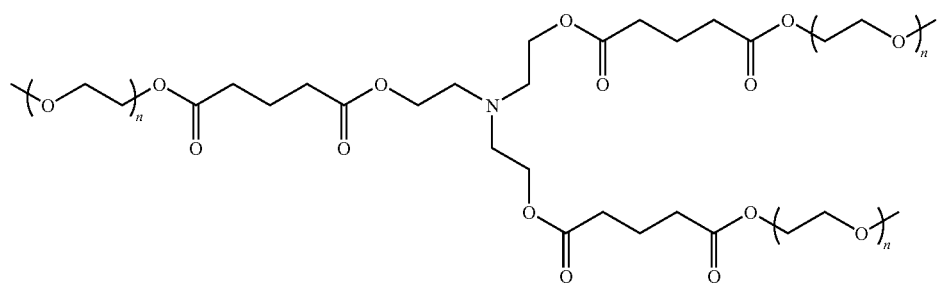
and
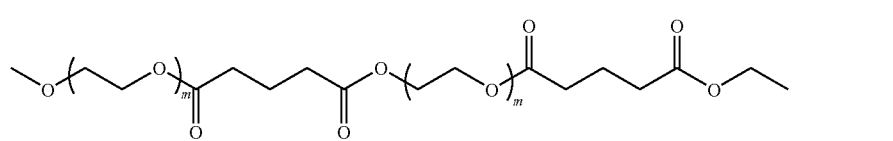

-continued

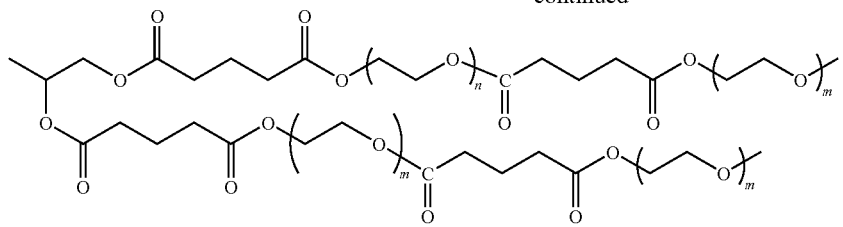

where n is from 2 to 250 and m is from 1 to 10.

5. The macromer or mixture of macromers of claim 1, where $R_3$ is the linear or branched residue of a water soluble polymer selected from the group consisting of a polyalkylene glycol, a polyalkylene oxide, polyvinylpyrolidone, poly(vinyl alcohol), poly(vinyl methyl ether), polyhydroxymethyl methacrylate, a polyacrylic acid polymer and copolymer, polyoxazoline, polyphosphazine, polyacrylamide, a polypeptide, and water soluble derivative thereof; and $R_4$ is the linear or branched organic residue selected from the group consisting of carboxylic acid-terminated polyalkylene glycol, diglycolic acid, malonic acid, succinic acid, glutaric acid, adipic acid, tartaric acid, citric acid, tricarballylic acid, glycerol triglutarate, pentaerythritol tetra glutarate, and erythritol.

6. A medically acceptable bioabsorbable tissue sealant and/or adhesive formulation comprising the macromer or mixture thereof of claim 1 and at least one solvent.

7. A method for sealing an internal wound comprising the steps of mixing the macromer or mixture of macromers of claim 1, or a composition comprising said macromer or mixture, with a solvent to obtain an adhesive composition; applying the adhesive composition to a wound; and allowing the adhesive composition to form an elastic gel.

8. The method for sealing an internal wound according to claim 7, wherein the adhesive composition is injectable via a syringe.

9. The method for sealing an internal wound according to claim 8, wherein the viscosity of the adhesive composition is from about 500 to 50,000 cP.

10. A medically acceptable bioabsorbable tissue sealant and/or adhesive formulation comprising the macromer or mixture thereof of claim 1 and at least one solvent, wherein c is 3.

11. A medically acceptable bioabsorbable tissue sealant and/or adhesive formulation comprising the macromer or mixture thereof of claim 1 and at least one solvent, wherein c is 4.

* * * * *